United States Patent
Conroy et al.

(10) Patent No.: US 11,173,300 B2
(45) Date of Patent: *Nov. 16, 2021

(54) PAIRED MEDICAL LEAD BODIES WITH CONDUCTIVE SHIELDS PROVIDING DESTRUCTIVE INTERFERENCE

(71) Applicant: MEDTRONIC, INC., Minneapolis, MN (US)

(72) Inventors: Mark J. Conroy, St. Louis Park, MN (US); Spencer Fodness-Bondhus, Columbia Heights, MN (US); Bryan D. Stem, Minneapollis, MN (US)

(73) Assignee: MEDTRONIC, INC., Minneapolis, MN (US)

(*) Notice: Subject to any disclaimer, the term of this patent is extended or adjusted under 35 U.S.C. 154(b) by 246 days.

This patent is subject to a terminal disclaimer.

(21) Appl. No.: 16/413,432

(22) Filed: May 15, 2019

(65) Prior Publication Data

US 2019/0308012 A1    Oct. 10, 2019

Related U.S. Application Data

(60) Division of application No. 15/910,655, filed on Mar. 2, 2018, now Pat. No. 10,293,156, which is a division of application No. 15/278,560, filed on Sep. 28, 2016, now Pat. No. 9,907,956, which is a continuation of application No. 14/395,219, filed as application No. PCT/US2013/023637 on Jan. 29, 2013, now Pat. No. 9,463,317.

(60) Provisional application No. 61/635,766, filed on Apr. 19, 2012.

(51) Int. Cl.
| | |
|---|---|
| *A61N 1/08* | (2006.01) |
| *A61N 1/37* | (2006.01) |
| *A61N 1/05* | (2006.01) |

(52) U.S. Cl.
CPC ............... *A61N 1/08* (2013.01); *A61N 1/05* (2013.01); *A61N 1/3718* (2013.01); *A61N 1/086* (2017.08)

(58) Field of Classification Search
CPC . A61N 1/05–06; A61N 1/086; A61B 5/04286
See application file for complete search history.

(56) References Cited

U.S. PATENT DOCUMENTS

| | | | | |
|---|---|---|---|---|
| 6,066,165 | A * | 5/2000 | Racz | A61N 1/05 607/117 |
| 6,587,733 | B1 * | 7/2003 | Cross, Jr. | A61N 1/0551 607/116 |
| 7,294,785 | B2 * | 11/2007 | Uutela | A61B 5/303 174/74 R |

(Continued)

*Primary Examiner* — Eugene T Wu
(74) *Attorney, Agent, or Firm* — Withers & Keys, LLC

(57) ABSTRACT

Medical lead bodies that are paired each include a braided conductive shield. The braided conductive shield of one lead body has a value for a physical parameter that differs from a value for the physical parameter of the second lead body. The difference in values of the physical parameter for the paired lead bodies results in a reduction in heating from exposure of the lead bodies to radiofrequency energy at electrodes associated with the lead bodies. The lead bodies may be paired by being implanted adjacently to one another. The lead bodies may be further paired by being coupled to a same distal body, such as a paddle containing the electrodes.

20 Claims, 10 Drawing Sheets

(56) References Cited

U.S. PATENT DOCUMENTS

| | | | | |
|---|---|---|---|---|
| 2003/0144719 A1* | 7/2003 | Zeijlemaker | ............ | A61N 1/05 607/122 |
| 2003/0204228 A1* | 10/2003 | Cross, Jr. | ............ | A61N 1/0553 607/116 |
| 2005/0004639 A1* | 1/2005 | Erickson | ............ | A61N 1/0551 607/122 |
| 2007/0255373 A1* | 11/2007 | Metzler | ............ | A61N 1/0553 607/117 |
| 2010/0070010 A1* | 3/2010 | Simpson | ............ | A61N 1/0553 607/117 |
| 2012/0157808 A1* | 6/2012 | Weiss | ............ | A61N 1/056 600/373 |

* cited by examiner

PAIRED MEDICAL LEAD BODIES WITH CONDUCTIVE SHIELDS PROVIDING DESTRUCTIVE INTERFERENCE

RELATED APPLICATIONS

The present application is a divisional application of U.S. application Ser. No. 15/910,655, filed on Mar. 2, 2018, which is a divisional application of U.S. Pat. No. 9,907,956, filed on Sep. 28, 2016, which is a continuation application of U.S. Pat. No. 9,763,317, filed on Oct. 17, 2014, which is a U.S. national phase filing of PCT/US2013/023637, filed on Jan. 29, 2013, which claims priority to U.S. Provisional App. No. 61/635,766 filed on Apr. 19, 2012.

TECHNICAL FIELD

Embodiments relate to medical leads that have braided conductive shields. More particularly, embodiments relate to medical lead bodies with braided conductive shields where the medical lead bodies are paired and where the braided conductive shields have different physical parameter values.

BACKGROUND

Medical leads provide electrical stimulation from a medical device to a target site within a body of a patient. The medical device is typically implanted or otherwise installed on the body in an accessible area at some distance from the target site, and the medical lead is routed to the target site either through a percutaneous procedure or by surgical implantation depending upon the type and size of the medical lead being implanted.

An issue occurs when the patient is subjected to radiofrequency (RF) electromagnetic energy in excess of the ambient, such as when having a magnetic resonance imaging (MRI) scan. The metal filars within the lead have current induced by the RF energy. This induced current can produce heating within the medical lead and at the electrodes which can cause harm to the patient. A shield may be included within the lead to limit the amount of current induced on the filars and thereby reduce heating at the electrodes.

In some cases, multiple lead bodies may be paired. For instance, the multiple lead bodies may be positioned adjacently when implanted. One particular example of such positioning is for surgical leads that utilize two lead bodies to carry stimulation signals to a distal paddle. Both lead bodies may include identical braided conductive shields to limit the amount of heating. While the amount of heating at the electrodes may be reduced by the presence of the identical braided conductive shields, it may be desirable to reduce the amount of heating by an even greater amount to allow for even greater scan power levels.

SUMMARY

Embodiments address issues such as these and others by providing paired lead bodies with braided conductive shields having different physical parameter values. The different physical parameter values for the paired leads result in an increased reduction of heating at the electrodes relative to identical braided conductive shields. The physical parameter may be one of a variety of different physical characteristics such as the weave density, weave angle, number of braid wires, braid diameter, and/or braid wire conductivity. The lead bodies may be paired by being aligned adjacently and in close proximity for at least a portion of their length, where this may be achieved through in various manners such as by positioning during implantation and/or by bonding of the lead bodies.

Embodiments provide a medical lead that includes a first lead body housing a first filar connected to a first proximal contact on the first lead body. The first lead body has a first braided conductive shield with a first value for a first physical parameter. The medical lead includes a second lead body housing a second filar connected to a second proximal contact on the second lead body, the second lead body having a second braided conductive shield with a second value for the first physical parameter that is different from the first value. The medical lead also includes a body housing a plurality of electrodes, the body being coupled to the distal end of the first and second lead bodies with a first electrode of the plurality connected to the first filar and a second electrode of the plurality connected to the second filar.

Embodiments provide a medical system that includes a first lead body housing a first filar connected to a first proximal contact on the first lead body. The first lead body has a first braided conductive shield with a first value of a first physical parameter, and the first lead body has a first electrode connected to the first filar. The medical system includes a second lead body housing a second filar connected to a second proximal contact on the second lead body. The second lead body has a second braided conductive shield with a second value of the first physical parameter that is different than the first value, and the second lead body has a second electrode connected to the second filar. The second lead body is positioned adjacently to the first lead body.

Embodiments provide a method of implanting a medical system that involves providing a first lead body housing a first filar connected to a first proximal contact on the first lead body. The first lead body has a first braided conductive shield with a first value of a first physical parameter. The method further involves providing a second lead body housing a second filar connected to a second proximal contact on the second lead body. The second lead body has a second braided conductive shield with a second value of the first physical parameter that is different than the first value. A body houses a plurality of electrodes and the body is coupled to the distal end of the first and second lead bodies with a first electrode of the plurality connected to the first filar and a second electrode of the plurality connected to the second filar. The method further involves implanting the first lead body and the second lead body such that the second lead body is positioned immediately adjacent to the first lead body.

Embodiments provide a method of implanting a medical system that involves providing a first lead body housing a first filar connected to a first proximal contact on the first lead body. The first lead body has a first braided conductive shield with a first value of a first physical parameter, and the first lead body has a first electrode connected to the first filar. The method further involves providing a second lead body housing a second filar connected to a second proximal contact on the second lead body. The second lead body has a second braided conductive shield with a second value of the first physical parameter that is different than the first value, and the second lead body has a second electrode connected to the second filar. The method further involves implanting the first lead body and the second lead body such that the second lead body is positioned immediately adjacent to the first lead body.

DETAILED DESCRIPTION

Embodiments provide paired medical lead bodies that have braided conductive shields with different physical parameter values. This difference in the braided conductive shields results in reduced heating at the electrodes associated with the paired medical lead bodies. The medical lead bodies may be paired by extending to a same paddle attached to the distal ends of both lead bodies. The medical lead bodies may also be paired by being positioned during implantation immediately adjacent to one another without the distal ends necessarily being connected to a same paddle.

The pairing of the lead bodies may also be accomplished by creating a bond between the lead bodies such as by gluing or melting the lead bodies together or by surrounding both lead bodies with tubing such as a heat shrink layer or an additional outer jacket. Such bonding provides the advantages of not requiring the surgeon to properly position the lead bodies to create the pairing and also by improving the predictability of the performance of the pairing.

Figure 1:
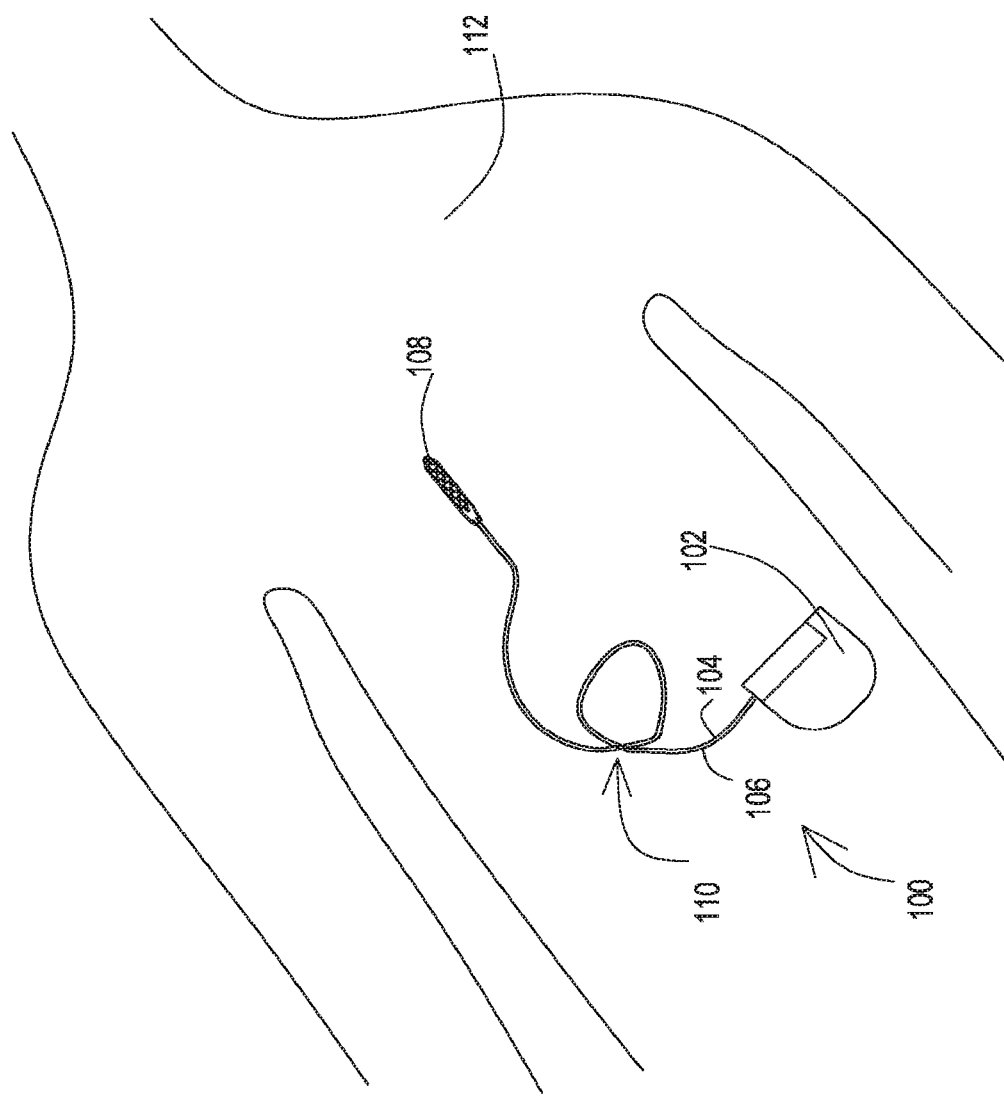
FIG. 1 shows an example of a medical system environment where a medical load includes paired lead bodies having braided conductive shields with different weave densities.

FIG. 1 shows one example of a medical system 100 that is implanted within a body 112 of a patient. The medical system 100 includes a stimulation device 102 that produces stimulation signals. First and second lead bodies 104, 106 have proximal ends that are coupled to the stimulation device 102. Distal ends of the first and second lead bodies 104, 106 are coupled to a paddle 108 which includes electrodes that deliver the stimulation signals to the body 112.

In this particular example, the first and second lead bodies 104, 106 are implanted such that they remain immediately adjacent to one another from proximal to distal ends. This adjacency allows the braided conductive shields of the first and second lead bodies 104, 106 to electrically couple in the presence of substantial levels of RF energy as might be encountered during an MRI scan. Such an RF coupling of thee shields from the adjacency of the lead bodies 104, 106 combined with the physical parameter value differences present between the braided conductive shields reduces the amount of heating that occurs at the electrodes of the paddle 108 during exposure to the RF energy. Without being bound by any particular theory, it is believed that the coupling of the shields where the shields have physical parameter value differences results in destructive interference of the RF waves present on the shields.

In this example, a strain relief loop 110 is also formed by the lead bodies 104, 106. The loop 110 provides slack to reduce strain on the lead bodies 104, 106 during bodily movements by the patient. As shown, the lead bodies 104, 106 maintain their adjacent relationship within the loop 110 and thus retain the RF coupling from the proximal to distal ends that reduces the electrode heating.

Figure 2:
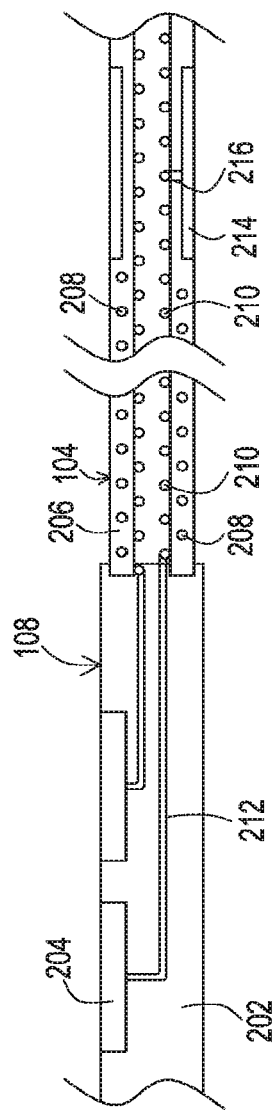
FIG. 2 shows a cross-sectional side view of a medical lead body.

FIG. 2 shows a cross-sectional side view of the paddle 108 and lead body 104 from the medical system 100 of FIG. 1. The paddle 108 is former by a body 202 that houses a collection of electrodes 204. The body 202 may be constructed in the conventional manner and from conventional paddle materials such as silicone or polyurethane.

The lead body 104 includes a jacket body 206 that extends from the proximal to distal ends. The jacket body 206 provides structural support while protecting the braided shield and conductors from external conditions. The jacket body 206 may be constructed of materials such as silicone or polyurethane.

Shield wires 208 are embedded within the jacket body 206. These shield wires 208 form a braid that ultimately shields conductive filars 210 from the RF energy to reduce the amount of current induced on the filars 210. The shield wires 208 may be constructed of various biocompatible conductors such as tantalum, titanium, MP35N, platinum, niobium, and the like.

The filars 210 are housed by the tubular body 206 and are surrounded by the shield wires 208. While the filars 210 are shown in a coiled configuration in this cross-sectional view, they may be in other configurations as well such as linear cables. The coiled filars 210 are electrically connected via a jumper portion 216 to contacts 214 that are positioned on a proximal end of the lead body 104. The coiled filars 210 are electrically connected via a jumper portion 212 to the electrodes 204 within the body 202 of the paddle 108. The filars may be constructed of biocompatible conductors such as MP35N, titanium molybdenum, platinum, and the like.

While FIG. 2 shows the coupling of the lead body 104 to the paddle body 108, it will be appreciated that the lead body 106 is also coupled to the paddle body 108 in the same manner. Therefore, the discussion with respect to the construction of the lead body 104 and the coupling of the lead body 104 to the body 108 equally apply to the lead body 106.

FIGS. 3-10 show various examples of paired lead bodies 104, 106. The lead bodies 104, 106 of these various examples may be constructed in various manners, such as those discussed above with respect to FIG. 2. Furthermore, in each of these examples, the filars present within the lead bodies 104, 106 may have various configurations, such as being coiled as shown above in FIG. 2 or the filars may be linear.

Figure 3:
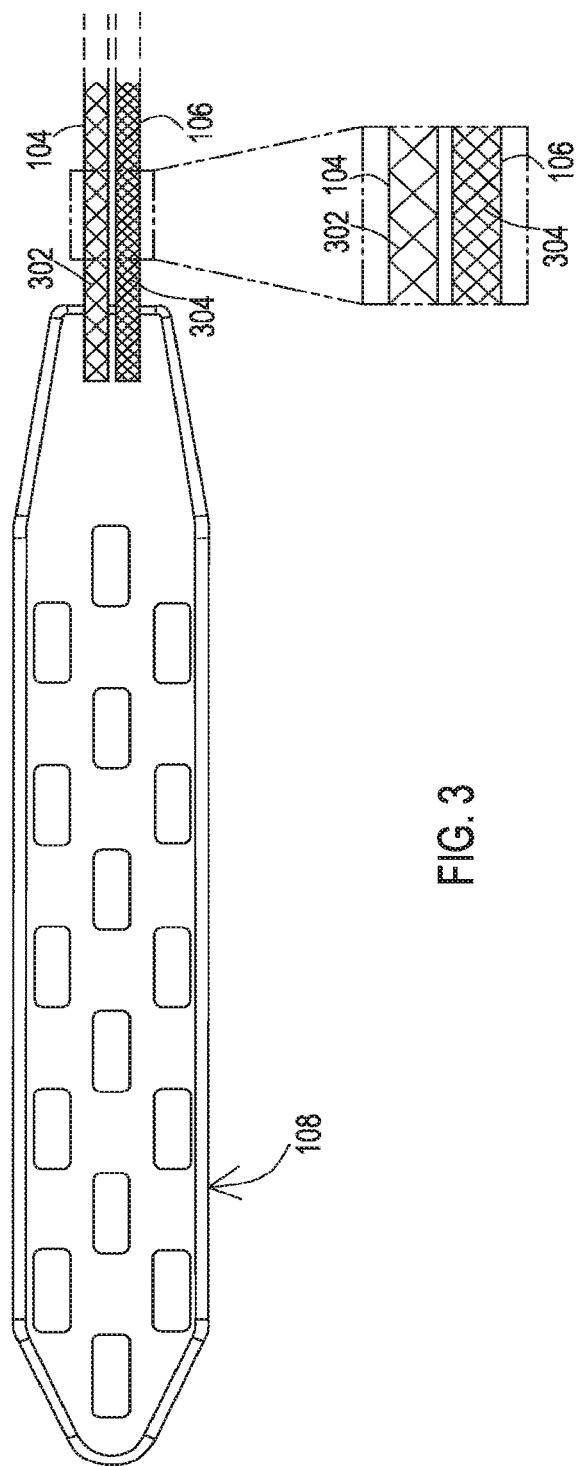
FIG. 3 shows one example of a medical lead having lead bodies with shields that have different numbers of wires and weave densities with even spacing of braid wires.

FIG. 3 shows an example of lead bodies 104, 106 connected to a paddle 108. The lead body 104 includes a braided conductive shield 302, and a lead body 106 that includes a braided conductive shield 304. The braided shield 302 differs from the braided shield 304 by having different values for at least one physical parameter that results in reduced heating at the electrodes of the paddle 108. In this particular example, there are multiple physical parameters that differ, including the number of wires and the weave density, which is the percentage of coverage by the shield material. The weave density difference in this example is provided by a difference in a pic rate, which is the number of braid wire intersections or pics per unit length of the lead body along a given axial line. Here, the braided shield 304 has more braid wires and a higher pic rate than the braided shield 302.

In one specific example, the shield 302 is a 100 pics per inch shield having 8 braid wires, 4 in each direction, while the shield 304 is a 200 pics per inch shield with 16 braid wires, 8 in each direction. In another specific example, the shield 302 is a 75 pics per inch shield while the shield 304 is a 134 pics per inch shield. The particular combination of pic rates between the two shields 302, 304 may be selected based on the combination of all physical characteristics that are present within the lead, including such characteristics as the overall length of the lead bodies 104, 106. Another factor that affects the performance of a given combination of physical parameter values relative to lead bodies having identical shields is the frequency of the RF energy being applied. The optimized combination can be found through empirical studies for a given lead design.

For example, one scenario to consider is a 64 MHz RF field with the electrodes being located approximately 20 cm from the top of the head of the patient, with the center of the MRI coil being 30 cm from the top of the head of the patient. With all else being essentially equal between the lead bodies 104, 106 and the shields 302, 304, it has been found that a 75/134 pics per inch shield combination produces less heating at the electrodes than a 100/200 pics per inch shield combination for 50 cm, 60 cm, and 100 cm lead lengths. However, it has been found that a 100/200 pics per inch shield combination produces less heating at the electrodes than a 75/134 pics per inch shield combination for 80 cm and 90 cm lead lengths.

In other examples where the weave density is different for the braided shields 302, 304, other physical parameters of the braided shields 302, 304 may have the same values or may be different. For instance, both shields 302, 304 may be constructed of the same material such as tantalum wires or may be constructed of different materials such as tantalum wires in one shield and titanium wires in the other.

Figure 4:
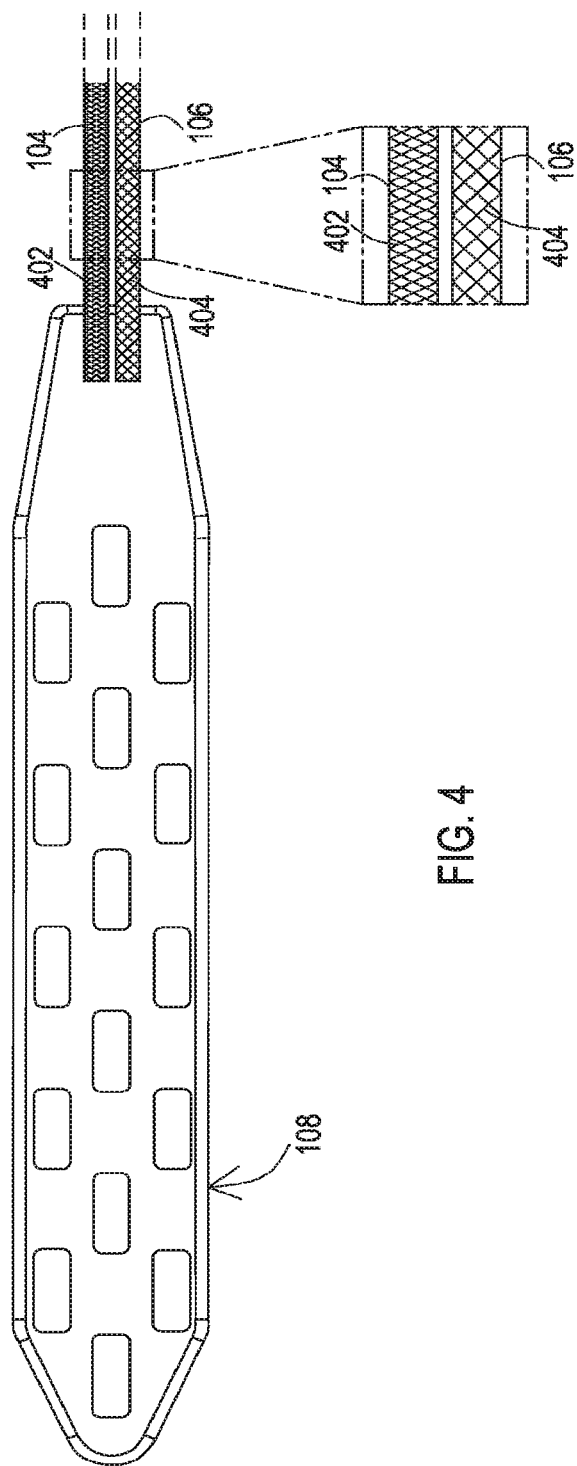
FIG. 4 shows one example of a medical lead having lead bodies with shields that have different weave angles and weave densities.

FIG. 4 shows another example of lead bodies 104, 106 connected to a paddle 108. The lead body 104 includes a braided conductive shield 402, and a lead body 106 that includes a braided conductive shield 404. The braided shield 402 of this example differs from the braided shield 404 by having different values for at least one physical parameter that results in reduced heating at the electrodes of the paddle 108. In this particular example, the physical parameters that differ include the weave angle, which is the angle formed by the braid wires relative to either a longitudinal or lateral dimension of the lead body, and the weave density or pic rate.

In other examples, other physical parameters of the braided shields 402, 404 may have the same values or may be different. For instance, both shields 402, 404 may be constructed of the same material such as tantalum wires or may be constructed of different materials such as tantalum wires in one shield and titanium wires in the other.

Figure 5:
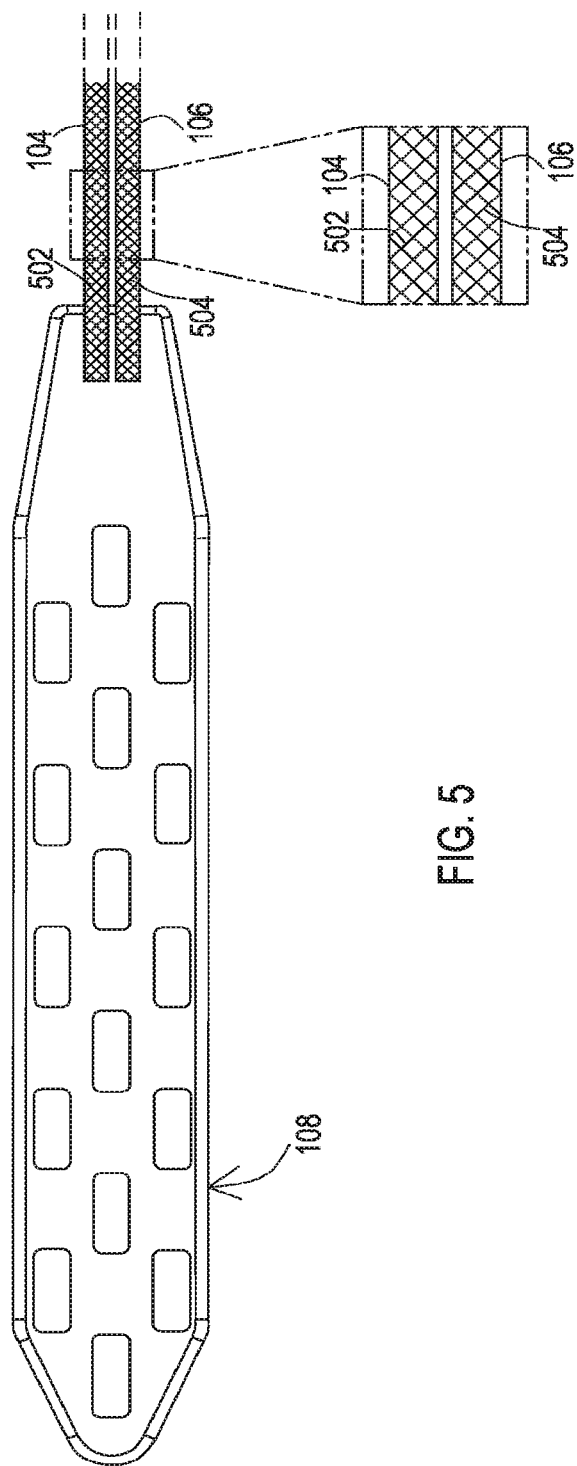
FIG. 5 shows one example of a medical lead having lead bodies with shields that are constructed of braid wire materials with different conductivities.

FIG. 5 shows another example of lead bodies 104, 106 connected to a paddle 108. The lead body 104 includes a braided conductive shield 502, and a lead body 106 that includes a braided conductive shield 504. The braided shield 502 differs from the braided shield 504 by having different values for at least one physical parameter. In this particular example, the physical parameters that differ include the braid material and hence the conductivity of the braid wire. For instance, the shield 502 may be constructed of tantalum while the shield 504 may be constructed of titanium, thereby providing the shields 502, 504 with different values of conductivity.

In other examples where the conductivity differs for the braided shields 502, 504, other physical parameters of the braided shields 502, 504 may have the same values or may be different. For instance, both shields 502, 504 may have the weave density as shown in FIG. 5 or the weave density may be different. Likewise, the weave angle may be the same for both shields 502, 504 as shown in FIG. 5 or may be different. The number of wires used for each of the shields 502, 504 may be the same or may be different. The diameter of the shields 502, 504 may be the same or may be different.

Figure 6:
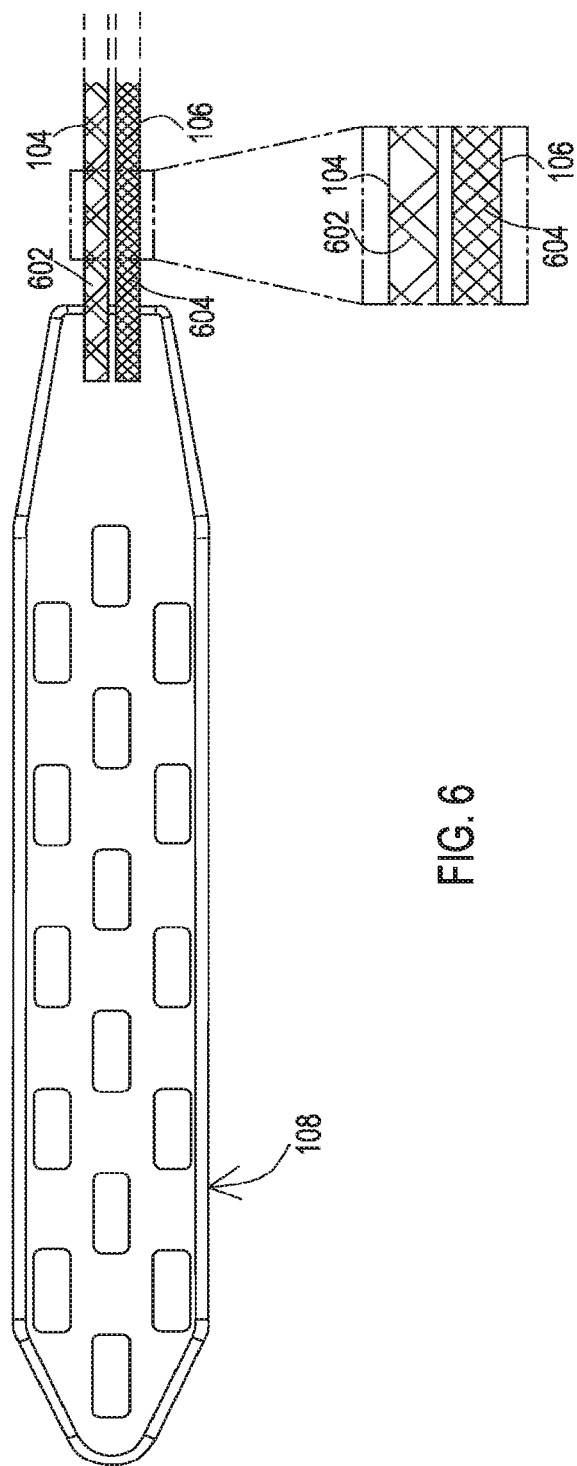
FIG. 6 shows one example of a medical lead having lead bodies with shields that have different numbers of wires and weave densities with uneven spacing of braid wires.

FIG. 6 shows another example of lead bodies 104, 106 connected to a paddle 108. The lead body 104 includes a braided conductive shield 602, and a lead body 106 that includes a braided conductive shield 604. The braided shield 602 differs from the braided shield 604 by having different values for at least one physical parameter. In this particular example, the physical parameters that differ include the number of braid wires that are present where shield 602 has a total of 8 wires with 4 in one direction and 4 in the other. Also, the weave density is lower and in this case the spacing is such that the 4 wires in each direction are grouped into pairs with spacing between pairs being greater than the spacing between each wire of a pair.

Figure 7:
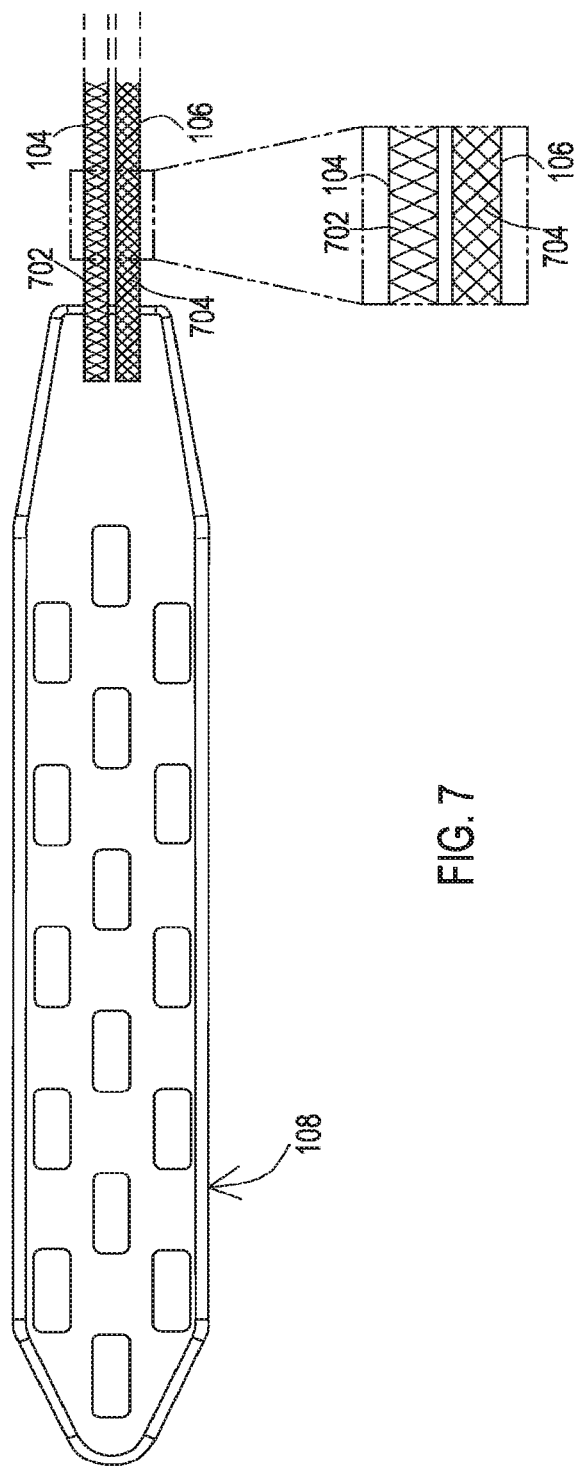
FIG. 7 shows one example of a medical lead having lead bodies with shields that have different numbers of wires and weave angles.

FIG. 7 shows another example of lead bodies 104, 106 connected to a paddle 108. The lead body 104 includes a braided conductive shield 702, and a lead body 106 that includes a braided conductive shield 704. The braided shield 702 differs from the braided shield 704 by having different values for at least one physical parameter. In this particular example, the physical parameters that differ include the number of braid wires that are present where shield 702 has a total of 8 wires with 4 in one direction and 4 in the other. Also, the weave angle relative to the lateral axis is lower.

Figure 8:
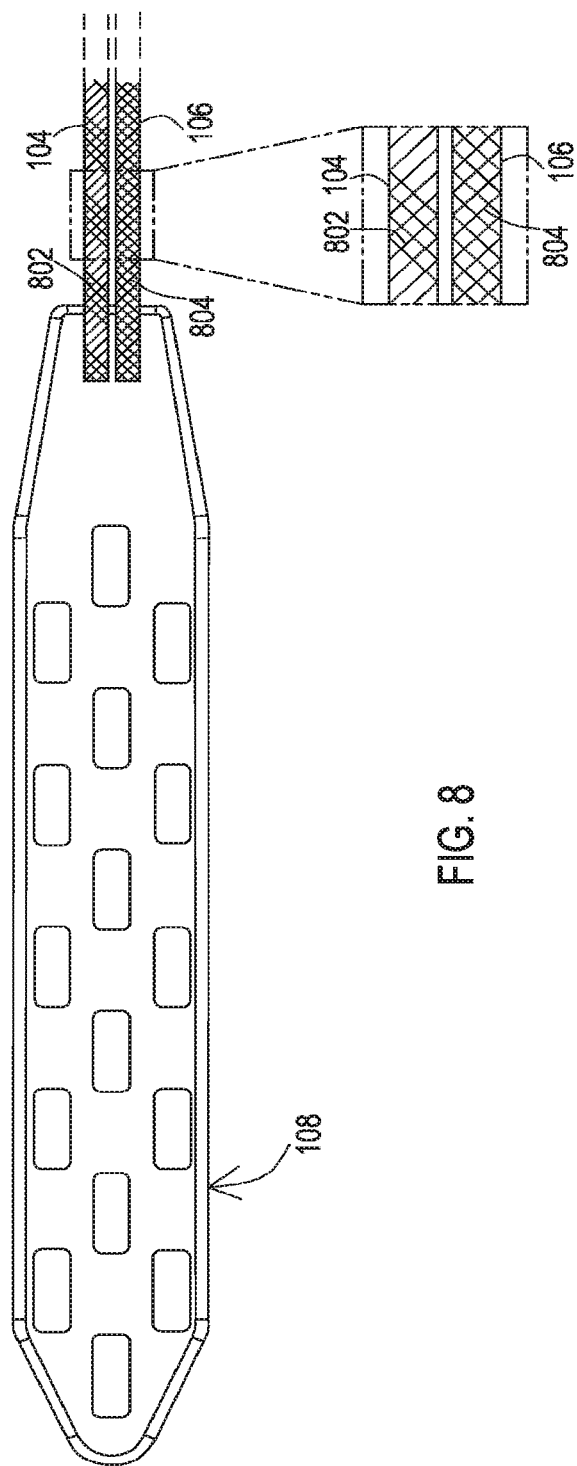
FIG. 8 shows one example of a medical lead having lead bodies with shields that have different numbers of wires where one lead body has an asymmetric wire count and that have different weave densities.

FIG. 8 shows another example of lead bodies 104, 106 connected to a paddle 108. The lead body 104 includes a braided conductive shield 802, and a lead body 106 that includes a braided conductive shield 804. The braided shield 802 differs from the braided shield 804 by having different values for at least one physical parameter. In this particular example, the physical parameters that differ include the number of braid wires that are present where shield 802 has a total of 12 wires with 8 in one direction and 4 in the other. As shown, the spacing between each turn of the group of 4 wires is by a greater amount than the spacing between each wire of the group.

Figure 9:
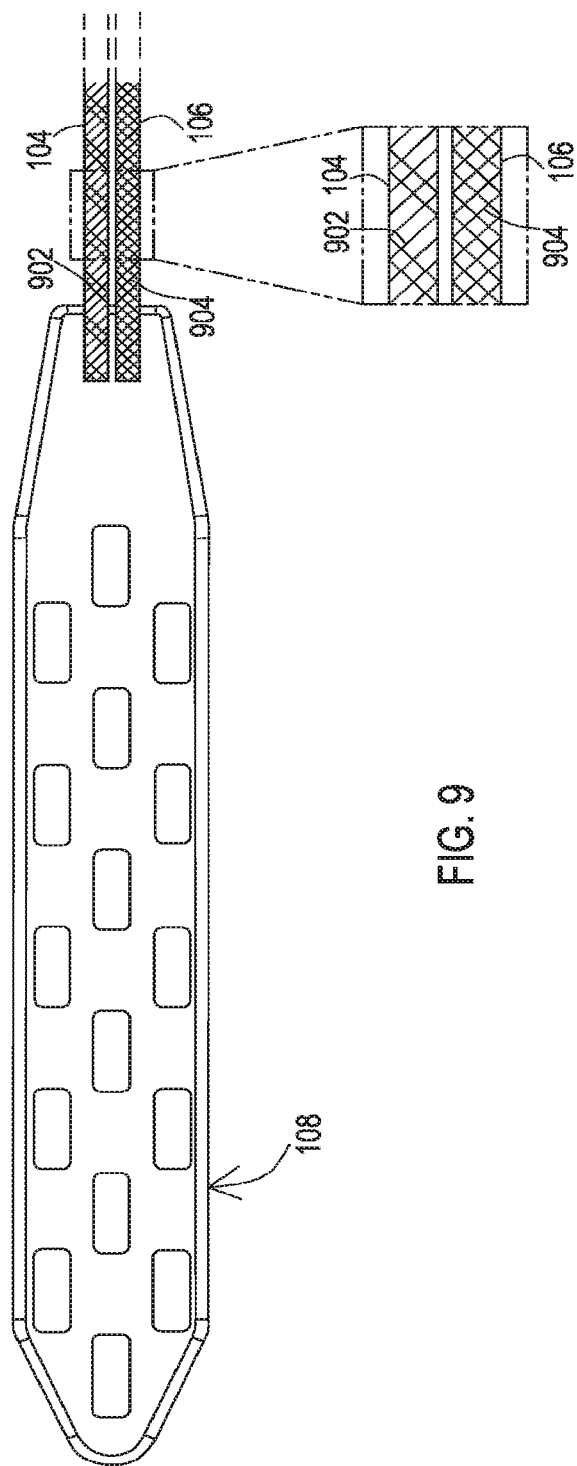
FIG. 9 shows one example of a medical lead having lead bodies with shields that have different numbers of wires where one lead body has an asymmetric wire count and that have different weave densities with uneven spacing of braid wires.

FIG. 9 shows another example of lead bodies 104, 106 connected to a paddle 108. The lead body 104 includes a braided conductive shield 902, and a lead body 106 that includes a braided conductive shield 904. The braided shield 902 differs from the braided shield 904 by having different values for at least one physical parameter. In this particular example, the physical parameters that differ include the number of braid wires that are present where shield 902 has a total of 8 wires with 4 in one direction and 4 in the other.

Also, the weave density is lower and in this case the spacing between pairs is greater than the spacing between each wire of a pair.

Figure 10:
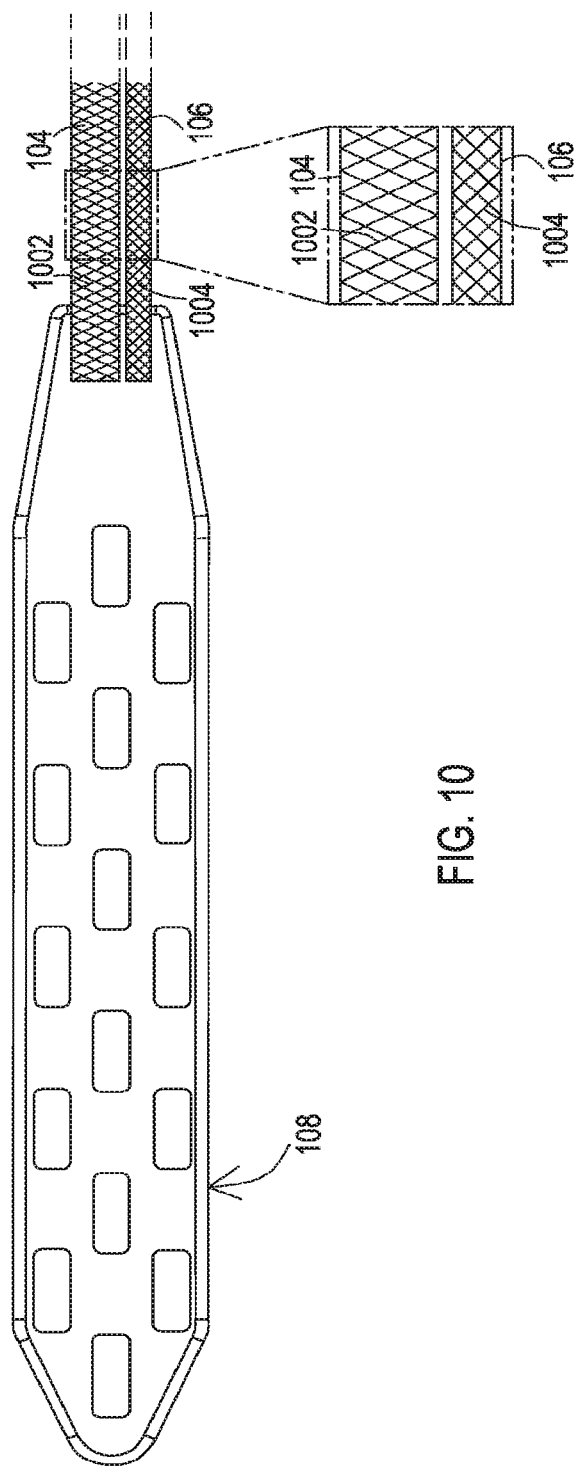
FIG. 10 shows one example of a medical lead having lead bodies with shields that have different diameters and weave angles.

FIG. 10 shows another example of lead bodies 104, 106 connected to a paddle 108. The lead body 104 includes a braided conductive shield 1002, and a lead body 106 that includes a braided conductive shield 1004. The braided shield 1002 differs from the braided shield 1004 by having different values for at least one physical parameter. In this particular example, the physical parameters that differ include diameter of the shield 1002 with a lower weave angle relative to the axial dimension. Also, the weave density is lower and in this case the spacing is uneven by having the 4 wires in each direction grouped into pairs with spacing between pairs being greater than the spacing, between the each wire of a pair.

While embodiments have been particularly shown and described, it will be understood by those skilled in the art that various other changes in the form and details may be made therein without departing from the spirit and scope of the invention.

What is claimed is:

1. A medical lead, comprising:
   a first lead body housing a first filar connected to a first proximal contact on the first lead body, the first lead body having a first conductive shield;
   a second lead body housing a second filar connected to a second proximal contact on the second lead body, the second lead body having a second conductive shield, the second lead body being adjacent to the first lead body so that destructive interference of at least some radio frequencies occurs on the first filar and the second filar; and
   a body housing a plurality of electrodes, the body being coupled to the distal end of the first and second lead bodies with a first electrode of the plurality connected to the first filar and a second electrode of the plurality connected to the second filar.

2. The medical lead of claim 1, wherein at least one physical parameter of the first conductive shield is the same for the second conductive shield.

3. The medical lead of claim 2, wherein the first conductive shield and the second conductive shield comprise braided wires.

4. The medical lead of claim 3, wherein the at least one physical parameter comprises at least one of weave density, weave angle, shield diameter, braid wire conductivity, and number of braid wires.

5. The medical lead of claim 2, wherein the first and second conductive shields comprise tantalum.

6. The medical lead of claim 1, wherein the first conductive shield is embedded within the first lead body and the second conductive shield is embedded within the second lead body.

7. A medical system, comprising:
   a first lead body housing a first filar connected to a first proximal contact on the first lead body, the first lead body having a first conductive shield, the first lead body having a first electrode connected to the first filar; and
   a second lead body housing a second filar connected to a second proximal contact on the second lead body, the second lead body having a second conductive shield, the second lead body having a second electrode connected to the second filar, the second lead body being positioned adjacently to the first lead body so that destructive interference of at least some radio frequencies occurs on the first filar and the second filar.

8. The medical system of claim 7, further comprising a body housing the first and second electrodes, and wherein the distal ends of the first and second lead bodies are coupled to the body.

9. The medical system of claim 7, further comprising a stimulation device and wherein the first lead body and the second lead body are coupled to the stimulation device.

10. The medical system of claim 7, wherein at least one physical parameter of the first conductive shield is the same for the second conductive shield.

11. The medical system of claim 10, wherein the first conductive shield and the second conductive shield comprise braided wires.

12. The medical system of claim 11, wherein the at least one physical parameter comprises at least one of weave density, weave angle, shield diameter, braid wire conductivity, and number of braid wires.

13. The medical system of claim 10, wherein the first and second conductive shields comprise tantalum.

14. The medical system claim 7, wherein the first conductive shield is embedded within the first lead body and the second conductive shield is embedded within the second lead body.

15. A method of implanting a medical system, comprising:
   providing a first lead body housing a first filar connected to a first proximal contact on the first lead body, the first lead body having a first conductive shield, the first lead body having a first electrode connected to the first filar;
   providing a second lead body housing a second filar connected to a second proximal contact on the second lead body, the second lead body having a second conductive shield, the second lead body having a second electrode connected to the second filar; and
   implanting the first lead body and the second lead body such that the second lead body is positioned immediately adjacent to the first lead body so that destructive interference of at least some radio frequencies occurs on the first filar and the second filar.

16. The method of claim 15, wherein a body houses the first and second electrodes, and wherein the distal ends of the first and second lead bodies are coupled to the body.

17. The method of claim 15, further comprising coupling the proximal ends of the first and second lead bodies to a stimulation device.

18. The method of claim 15, wherein at least one physical parameter of the first conductive shield is the same for the second conductive shield.

19. The method of claim 18, wherein the first conductive shield and the second conductive shield comprise braided wires.

20. The method of claim 19, wherein the at least one physical parameter comprises at least one of weave density, weave angle, shield diameter, braid wire conductivity, and number of braid wires.

* * * * *